US010939933B2

(12) United States Patent
Truckai

(10) Patent No.: US 10,939,933 B2
(45) Date of Patent: Mar. 9, 2021

(54) SURGICAL DEVICE AND METHOD OF USE

(71) Applicant: Corinth MedTech, Inc., Cupertino, CA (US)

(72) Inventor: Csaba Truckai, Saratoga, CA (US)

(73) Assignee: Corinth MedTech, Inc., Cupertino, CA (US)

( * ) Notice: Subject to any disclaimer, the term of this patent is extended or adjusted under 35 U.S.C. 154(b) by 398 days.

(21) Appl. No.: 15/291,964

(22) Filed: Oct. 12, 2016

(65) Prior Publication Data

US 2017/0105748 A1 Apr. 20, 2017

Related U.S. Application Data

(60) Provisional application No. 62/241,351, filed on Oct. 14, 2015.

(51) Int. Cl.
*A61B 18/14* (2006.01)
*A61B 17/32* (2006.01)
*A61B 18/00* (2006.01)

(52) U.S. Cl.
CPC ...... *A61B 17/32002* (2013.01); *A61B 18/149* (2013.01); *A61B 18/1482* (2013.01);
(Continued)

(58) Field of Classification Search
CPC ............ A61B 17/32002; A61B 18/149; A61B 2017/32004; A61B 2018/00184; A61B 2018/00291; A61B 2018/00517; A61B 2018/00601; A61B 18/14; A61B 18/142; A61B 18/1442; A61B 18/1445; A61B 18/1448; A61B 18/1482; A61B 18/00184; A61B 18/00517; A61B 18/00547; A61B 18/00982; A61B 18/144
(Continued)

(56) References Cited

U.S. PATENT DOCUMENTS 7,744,595 B2 6/2010 Truckai et al.
8,221,404 B2 7/2012 Truckai
(Continued)

FOREIGN PATENT DOCUMENTS

CN 1602812 A 4/2005
CN 104093374 B 5/2017
WO WO-2017066321 A1 4/2017

OTHER PUBLICATIONS

International Search Report and Written Opinion dated Jan. 10, 2017 for International Application No. PCT/US2016/056640.
(Continued)

*Primary Examiner* — Michael F Peffley
*Assistant Examiner* — Khadijeh A Vahdat
(74) *Attorney, Agent, or Firm* — Wilson Sonsini Goodrich & Rosati

(57) ABSTRACT

A tissue resecting device includes an elongated shaft having a central axis, a distal end, and an outer surface. An offset housing is mounted on the distal of the shaft and has a tissue-receiving window. The tissue-receiving window is offset radially outwardly from the outer surface of the shaft, and a moveable electrode is configured to move back and forth across the window to resect tissue which extends into the window. The offset housing improves visibility of the cutting window when viewed from endoscopes and other visualization apparatus.

38 Claims, 7 Drawing Sheets

(52) U.S. Cl.
CPC ........... *A61B 2017/32004* (2013.01); *A61B 2018/00184* (2013.01); *A61B 2018/00517* (2013.01); *A61B 2018/00547* (2013.01); *A61B 2018/00982* (2013.01); *A61B 2018/144* (2013.01)

(58) Field of Classification Search
USPC .................................................. 606/28–50
See application file for complete search history.

(56) References Cited

U.S. PATENT DOCUMENTS

| | | | |
|---|---|---|---|
| 2004/0138655 | A1 | 7/2004 | McClurken et al. |
| 2005/0070889 | A1* | 3/2005 | Nobis ............ A61B 17/320016 606/45 |
| 2007/0213704 | A1 | 9/2007 | Truckai et al. |
| 2009/0018603 | A1 | 1/2009 | Mitelberg et al. |
| 2009/0270849 | A1 | 10/2009 | Truckai et al. |
| 2010/0305565 | A1 | 12/2010 | Truckai et al. |
| 2011/0196401 | A1* | 8/2011 | Robertson ...... A61B 17/320092 606/169 |
| 2013/0090642 | A1 | 4/2013 | Shadduck et al. |
| 2013/0296847 | A1* | 11/2013 | Germain ............ A61B 18/1206 606/39 |
| 2014/0303611 | A1 | 10/2014 | Shadduck et al. |
| 2014/0324065 | A1 | 10/2014 | Bek et al. |
| 2014/0336643 | A1 | 11/2014 | Orczy-Timko et al. |
| 2016/0361084 | A1* | 12/2016 | Weisenburgh, II ........................ A61B 18/1482 |

OTHER PUBLICATIONS

"Supplement European Search Report EP16853110 dated Mar. 5, 2019".

* cited by examiner

SURGICAL DEVICE AND METHOD OF USE

CROSS-REFERENCE TO RELATED APPLICATIONS

This application claims the benefit of Provisional No. 62/241,351 (Attorney Docket No. 42005-705.101), filed Oct. 14, 2015, the entire content of which is incorporated herein by reference.

BACKGROUND OF THE INVENTION

Field of the Invention

The present invention relates to devices and methods for resecting and removing tissue from the interior of a patient's body, for example in a transurethral resection of prostate tissue to treat benign prostatic hyperplasia.

Electrosurgical cutting devices often comprise a shaft or sleeve having a tissue extraction lumen with one or more radio frequency (RF) cutting blades arranged to resect tissue which may then be drawn into the extraction lumen, often via vacuum assistance through a cutting window. Most such electrosurgical tissue cutting devices rely on manually engaging the cutting window against the target tissue to be resected. While such manual engagement is often sufficient, in other cases, such as in laparoscopic procedures having limited access and field of view, the target tissue can be difficult to visualize prior to resection and, in particular, it can be difficult to assure that the optimum target site has been engaged by the cutting window. For these reasons, it would be desirable to provide improved electrosurgical cutting tools having improved visibility and ability engage and immobilize tissue prior to cutting and to extract the tissue from tools after cutting.

Related patents and published applications include U.S. Pat. Nos. 8,221,404; 7,744,595; U.S. Pat. Publ. 2014/0336643; U.S. Pat. Publ. 2010/0305565; U.S. Pat. Publ. 2007/0213704; U.S. Pat. Publ. 2009/0270849; and U.S. Pat. Publ. 2013/0090642.

SUMMARY OF THE INVENTION

In a first aspect of the present invention, a tissue resecting device comprises an elongated shaft having a central axis, a distal end, and an outer surface. An offset housing is mounted on the distal of the shaft and has a tissue-receiving window. The tissue-receiving window is offset radially outwardly from the outer surface of the shaft, and a moveable electrode is configured to move back and forth across the window to resect tissue which extends into the window. The offset housing improves visibility of the cutting window when viewed from endoscopes and other visualization apparatus.

In specific embodiments, the tissue resecting device may be adapted to oscillate laterally across the window. For example, a motor may be coupled to the moveable electrode to oscillate the moveable electrode laterally across the window at a rate ranging from 1 Hz to 50 Hz. The tissue resecting device may further comprise a negative pressure source communicating with the window through the shaft, and a controller may be adapted to control at least one of an electrical source coupled to the electrode, the motor coupled to the moveable electrode, and the negative pressure source. The controller may be further adapted to control fluid inflows from a fluid source to a resection site. The window is usually offset outwardly from said outer shaft surface by at least 2 mm, often at least 4 mm, and typically in a range from 2 mm and 12 mm.

In a second aspect of the present invention, a tissue resecting device comprises an elongated shaft extending about a central axis. A housing is attached to a distal end of the shaft and is positioned asymmetrically relative to the central axis. A moveable electrode configured to move in a back-and-forth stroke across a tissue-receiving window in the housing to resect tissue. The asymmetric housing improves visibility of the window and the ability of the moving electrode to resect tissue.

In specific embodiments, the asymmetric housing has an L-shape relative to the central axis. In further embodiments, the window in the asymmetric housing is aligned in parallel to the central axis and extends radially outwardly from an outer surface of the shaft. The electrode is typically adapted to move laterally across the window but alternatively could be adapted to move axially across the window. The tissue resecting device may further comprise a motor coupled to the moveable electrode to oscillate the moveable electrode across the window, and the motor may be configured to oscillate the moveable electrode at a rate ranging from 1 Hz to 50 Hz. The electrode typically moves in an arc, and a surface of the window has will usually have an arc shape more usually an arc shape congruous with the arc of electrode travel. The window may have a rectangular shape, for example with an axial dimension ranging from 2 mm to 20 mm., and/or a lateral dimension ranging from 2 mm to 10 mm. The window may have circumferentially or axially spaced-apart edges, and the electrode may be configured to move past those edges. Alternatively, the window may have at least two sides with ledges for receiving the electrode at the termination of its stroke.

In a third aspect of the present invention, a tissue resecting device comprises an elongated shaft extending within a cylindrical envelope. A distal end of the shaft is coupled to an offset housing having a tissue-receiving window. The window has a surface spaced radially outwardly from and oriented generally parallel to the cylindrical envelope. A moveable electrode is configured to move over the window surface and to resect tissue received through the window. As with previous aspects of the present invention, such structures improve visibility of the window and the ability of the moving electrode to resect tissue.

In specific embodiments, the tissue resecting device further comprises a motor coupled to the moveable electrode to oscillate the moveable electrode across the window. The motor may be configured to oscillate the moveable electrode at a rate ranging from 1 Hz to 50 Hz. The window is typically offset radially outwardly from said outer shaft surface by at least 2 mm, often by at least 4 mm, and usually in a range from 2 mm to 12 mm.

In a fourth aspect of the present invention, a tissue resecting device comprises an elongated shaft extending to a working end having a tissue-receiving window, said elongated shaft having an outer surface and said window having an exterior surface which is offset radially outwardly from the outer surface of the elongated shaft. A moveable electrode is configured to sweep across the exterior surface of the window. As with all prior aspects of the present invention described above, such structures improve visibility of the window and the ability of the moveable electrode to resect tissue.

In specific embodiments, the tissue resecting device further comprises a motor coupled to the moveable electrode to oscillate the moveable electrode across the window. The motor may be configured to oscillate the moveable electrode at a rate ranging from 1 Hz to 50 Hz. The exterior surface of the window typically extends laterally in an arc, and the electrode portion moves in an arc over the exterior surface. The window may have a rectangular plan shape with an axial dimension ranging from 2 mm to 20 mm and a lateral dimension ranging from 2 mm to 10 mm. The electrode is typically configured to move past lateral edges of the window when being swept across the exterior surface of the window. Alternatively, the window may have at least two sides with ledges for receiving the electrode at the termination of its stroke. The window is preferably within a housing portion that is offset outwardly from an outer surface of the shaft.

DETAILED DESCRIPTION OF THE INVENTION

Figure 1:
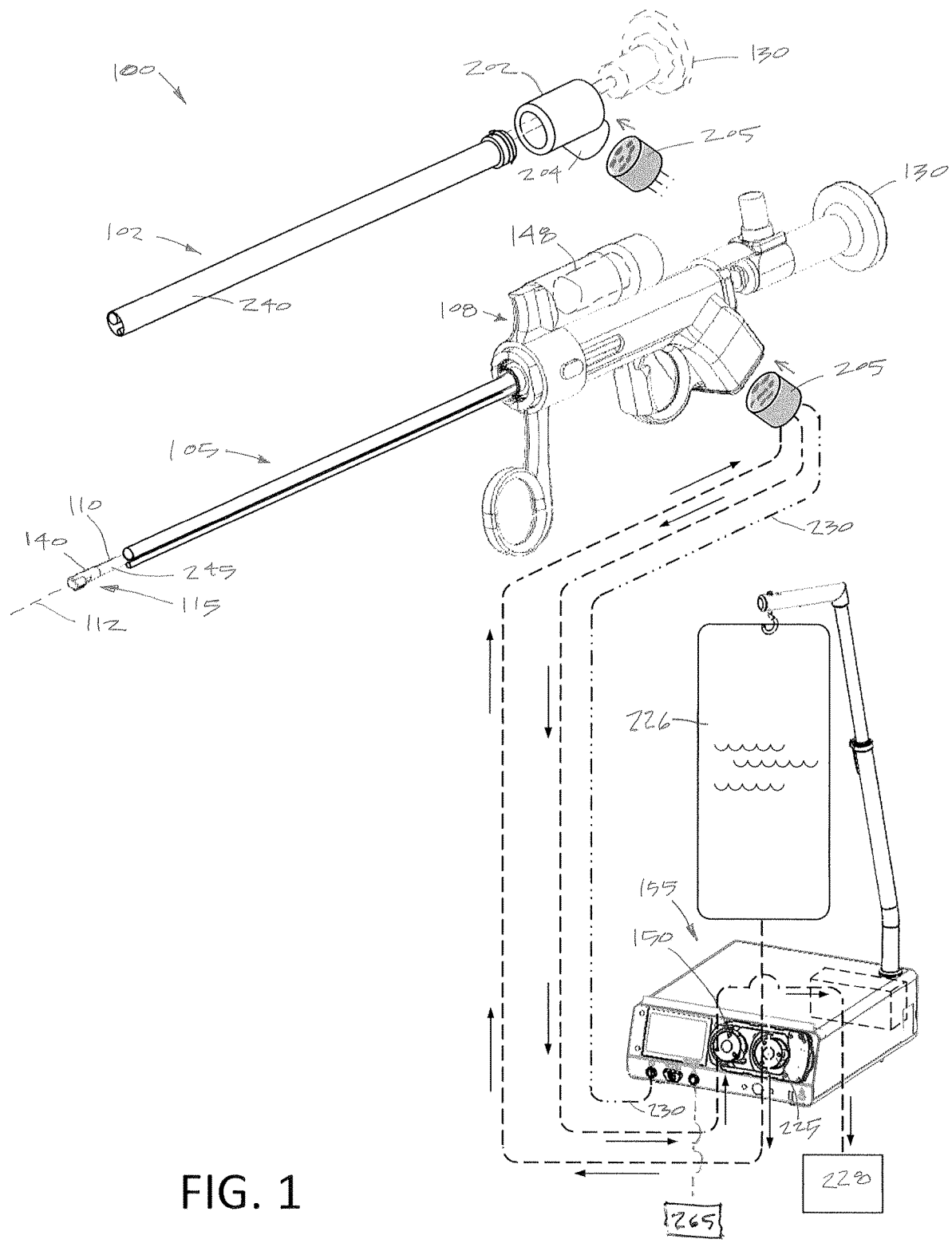
FIG. 1 is a view of a tissue resecting device and a block diagram of systems and operating components corresponding to the invention.

FIGS. 1 illustrates an electrosurgical tissue resecting system 100 for use in urological procedures to resect tissue that includes an introducer sleeve or sheath 102 and a hand-held single-use tissue resecting device or probe 105. The resecting device 105 has a handle portion 108 that is coupled to an elongated shaft or extension portion 110 that has an outer diameter ranging from about 2 mm to 7 mm, and in one variation is 5 mm in diameter. The shaft 110 extends about longitudinal axis 112 to a working end 115 that is radially asymmetric relative the shaft 110 and its axis 112 as further described below. In one variation, the device is adapted for performing a TURP procedure (transurethral resection of prostate) or a bladder tumor resection procedure and thus the shaft portion 110 extends about axis 112 with a length suitable for introducing in a transurethral approach to reach the targeted prostate tissue or bladder tissue.

As will be described below and shown in FIG. 1, the resecting device 105 is adapted for introduction through the introducer sleeve 102. Such an introducer sleeve 102 is adapted to receive a commercially available endoscope 130 as can be understood from FIG. 1.

Figure 2:
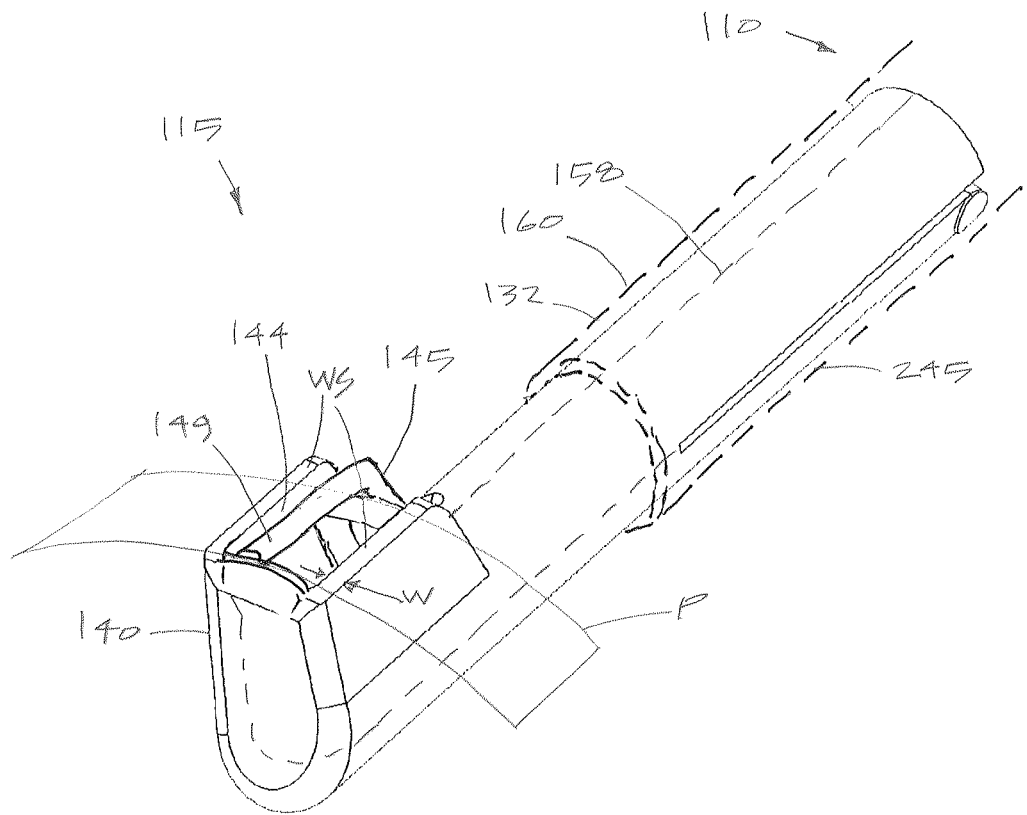
FIG. 2 is a perspective view of the working end of the resecting device of FIG. 1 showing an asymmetric ceramic housing and moving electrode that is adapted to sweep across a tissue-receiving window.
Figure 3:
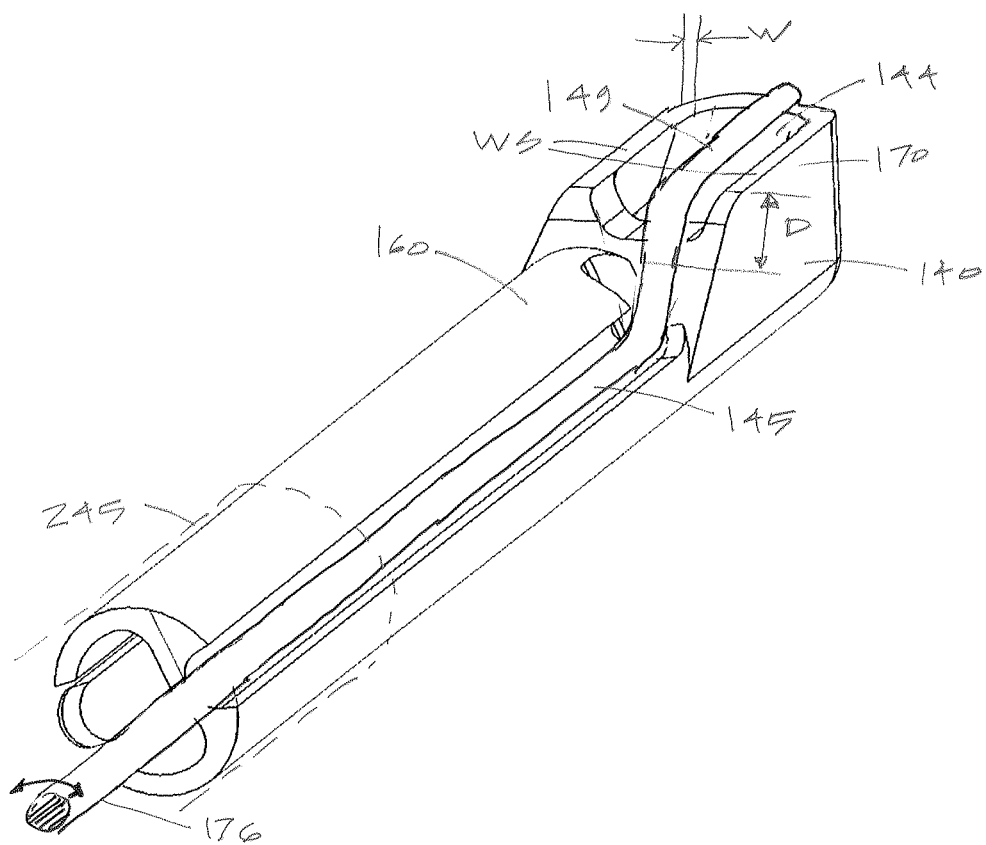
FIG. 3 is another perspective view of the working end of FIG. 2 from a different angle.

Referring to FIGS. 1-3, in general, it can be seen the resecting device 105 has an elongated shaft 110 that extends to a distal shaft portion 132 that is coupled to an offset resecting housing 140 that has an offset tissue-receiving window 144. A moveable electrode 145 is adapted to be driven by a motor drive unit 148 in handle 108 (see FIG. 1) so that the longitudinal portion 149 of the electrode 145 sweeps across the window 144 from side to side to electrosurgically resect tissue that is captured in the window 144. The targeted tissue can be suctioned into and captured in window 144 by means of a negative pressure source or outflow pump 150 in controller 155 that communicates with a tissue extraction channel 158 extending through the device 105 and terminating in the window 144.

Figure 4A:
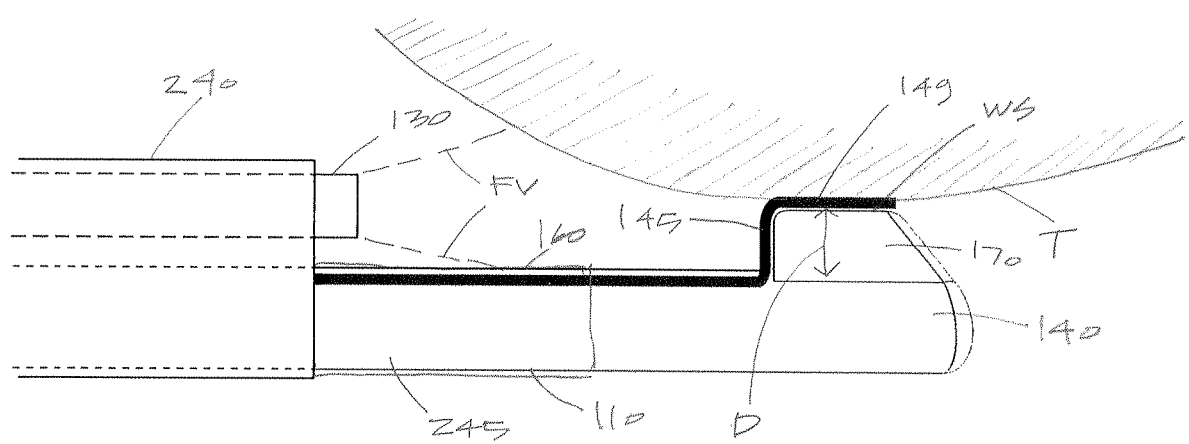
FIG. 4A is a schematic view of the working end of FIGS. 2-3 interfacing with tissue targeted for resection under endoscopic vision.

More in particular, referring to FIGS. 2 and 3, the configuration of the offset housing 140 is adapted to perform multiple functions. First, the offset housing 140 positions the window surface WS (within curved plane P indicated in FIG. 2) outwardly from the outer surface 160 of shaft 110 which then allows the window surface WS to be fully visible through a endoscope 130 or other viewing means that would be introduced parallel to the device shaft 110 (see FIG. 4A). For example, FIG. 4A is a schematic view of the working end 115 with working surface WS in contact with targeted tissue T. As can be seen in FIG. 4A, the endoscope 130 is positioned with the field of view FV directly aligned with the working surface WS thus allowing optimal viewing of the tissue resection process. The outer surface 160 typically defines a cylindrical envelope from which the offset housing 140 projects radially.

Figure 4B:
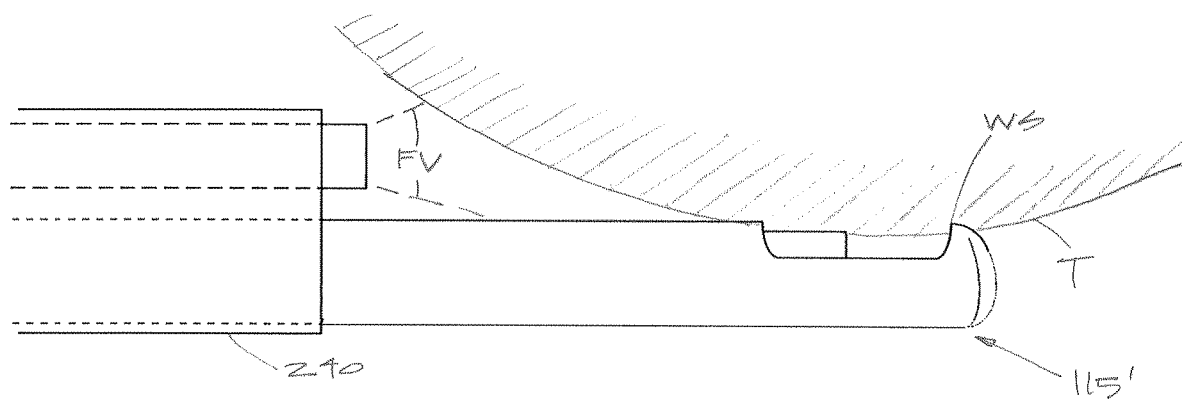
FIG. 4B is a schematic view of a working end of a prior art tubular cutting device used in a hypothetical resection procedure.

In contrast, FIG. 4B shows a working end 115' of a conventional dual sleeve tubular cutter having a window surface WS' which when pressed against an organ prevents endoscopic vision of the interface between the tubular cutting edge and the tissue T during a resection procedure.

Figure 5:
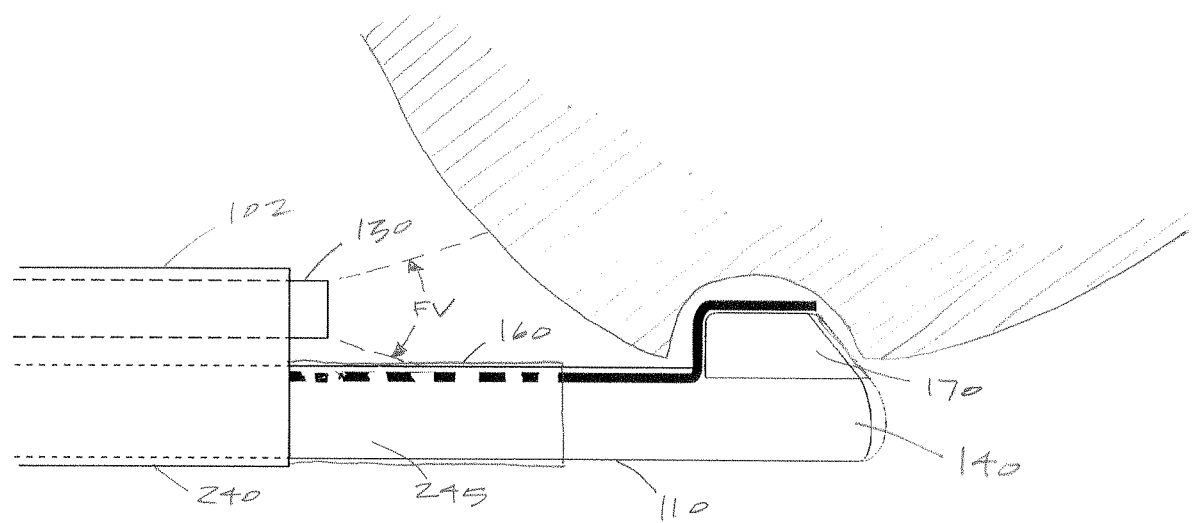
FIG. 5 is another schematic view of the working end of FIGS. 2-3 being used to resect targeted tissue to a significant depth from the organ surface.

Second, the offset housing 140 is adapted for resecting tissue to a greater depth in a localized region of an organ, rather than resecting surface tissues over a broad area. More in particular as shown in FIG. 5, the offset portion 170 of housing 140 can be pushed into tissue perpendicular to axis 112 of the probe shaft 110. Thus, as shown in FIG. 5, the offset housing 140 can be used to resect tissue deep into in a localized region that would not be possible with a resecting device having the configuration shown in FIG. 4B.

FIGS. 2 and 3 illustrate the asymmetric or offset dielectric housing 140 that can comprise a ceramic material such as zirconium oxide, aluminum oxide or similar materials as is known in the art. In FIGS. 2-3, it can be seen that window surface WS is offset from the shaft outersurface 160 by a predetermined dimension D which can be from 2 mm to 8 mm and in one embodiment comprises a 5 mm offset.

As can be further be seen in FIGS. 2-3, the width W of the window surface WS around at least portions of the perimeter of the window 144 is a limited dimension, for example less than 3 mm, or less than 2 mm or less than 1 mm. which allows the offset portion 170 of housing 140 to be pushed into tissue perpendicular to the device axis 112 as the electrode 145 sweeps across the window 144.

Referring to FIGS. 2-3, one variation of resecting device 105 has an electrode 145 that can be tungsten or stainless steel wire that with electrode portion 149 adapted to sweep across the window 144 at any suitable rate, for example from 1 Hz to 500 Hz. In FIG. 3, it can be understood that the electrode 145 has an elongated proximal shaft portion 176 that extends into handle 108 of the device (FIG. 1). The proximal end of electrode 145 is operatively coupled to a motor drive unit 148 and a suitable mechanism or controller is provided to move the elongated electrode proximal shaft portion 176 in an arc to resect tissue.

As can be understood from FIGS. 2-3, the electrode portion 149 moves back and forth akin to a windshield wiper across window 144 in the offset housing 140. A number of mechanisms can be used to effectuate the desired movements of the electrode, or the motor drive 148 simply can be controlled by software to move in intermittent clockwise and counter-clockwise directions. In one variation, the elongated electrode proximal shaft portion 176 of the electrode 145 will twist over its length and thus the motor drive 148 can be adapted to rotate the electrode shaft in an arc with radial angle which is greater than the window's comparable radial angle or arc. Thus, the electrode portion 149 can be expected to move back and forth entirely across the window even when meeting some tissue resistance by compensating for some twisting that is allowed in the elongated electrode proximal shaft portion 176. In one variation, the motor drive unit can be adapted to over-rotate the electrode shaft portion 176 at its proximal end by a selected amount which can be from 10° radial motion to 90° radial motion to compensate for twisting of the electrode shaft portion to insure that electrode portion 149 sweeps entirely across the surface of window 144.

Figure 6:
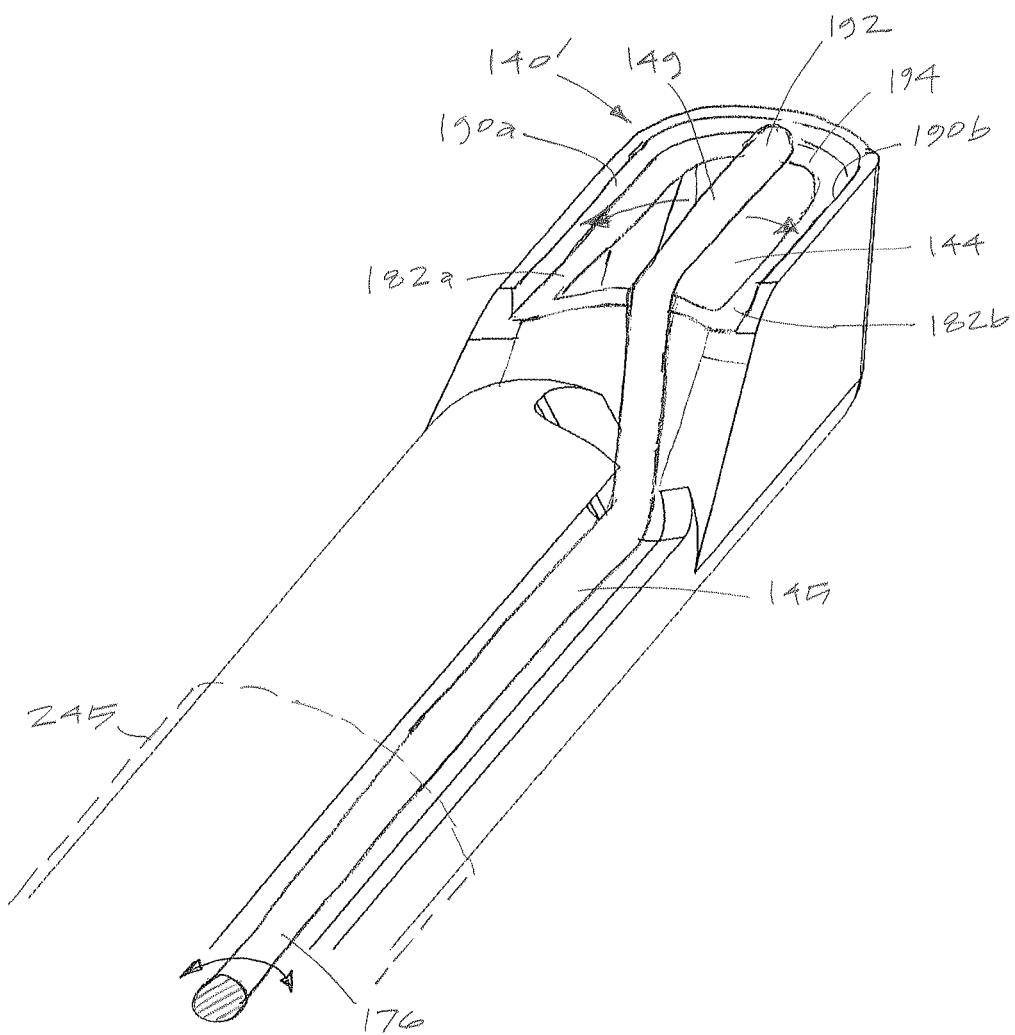
FIG. 6 is a perspective view of a distal dielectric housing of a working end similar to that of FIGS. 2-3 showing window sides with ledges for receiving the electrode at the ends of its movement in a sweeping arc.

In general, the window 144 in housing 140 can be configured to have a radial arc relative to the electrode shaft 176 ranging between 30° and 180°. In one variation of housing 140' shown in FIG. 6, it can be seen that the electrode portion 149 has a range of motion that extends across the radial dimension of the window 144 to ensure that any tissue captured in the window is resected as the electrode portion 149 passes the window edges 182a and 182b to function like a shear or in a scissor-like manner. The electrode portion 149 moves over ledges 186a and 186b on either side of the housing 140' and can bump into surfaces 190a and 190b. By bumping into the surfaces 190a and 190b, any over rotation in the electrode shaft 176 to accommodate twisting as described above can limit the rotation of the electrode portion in the housing 140'. Further, in FIG. 6, it can be seen that the distal tip 192 of electrode portion 149 extends distally beyond window 144 and onto distal ledge 194 in the housing 140' to ensure tissue is resected by the electrode in the distal window region.

Now turning back to FIG. 1, it can be understood that the resecting device 105 and endoscope 130 can be used with introducer sleeve assembly or sheath 102. As shown in FIG. 1, the introducer sleeve 102 has a proximal handle body 202 with a connector 204 that is adapted to couple to connector member 205. The connector 205 is adapted to couple to controller 155 and provide within a single cable a first lumen communicating with the fluid outflow pump 150, a second lumen communicating with a fluid inflow pump 225, and a third lumen communicating with a pressure sensor positioned in the controller 155 or in or near the connector 205. As can be seen in FIG. 1, the introducer sleeve 102 can also accommodate an endoscope 130. Thus, the introducer sleeve 120 can be assembled with the endoscope 130 (and without the reaction device 105) and coupled by connector 205 to the controller 155 to provide an inflow of irrigation fluid from fluid source 226, and outflow of irrigation fluid to collection reservoir 228 together with pressure sensing to allow the assembly to be used in a diagnostic procedure prior to a tissue resection procedure. In other words, the introducer sleeve 102 can function as a 'continuous flow' optical introducer for use in trans-urethral access to a targeted sire in the prostate or bladder.

After the introducer sleeve assembly 102 is used for an initial diagnostic procedure, the endoscope 130 can be removed from the assembly 102 and connector 205 can be disconnected from handle body 205. Thereafter, the sleeve portion 240 (see FIG. 1) of introducer assembly 102 can be detached from proximal handle body 204 with the sleeve portion 240 remaining in the patient. Next, the endoscope 130 and connector 205 can be assembled with the resecting device 105 and the physician cam insert the resecting device 105 through the sleeve portion 240 remaining in the patient to access the targeted site. The resecting device 105 and sleeve portion 204 in combination then provide lumens as described above for fluid inflows, fluid outflows and direct pressure sensing through lumens in connector 205.

In another variation, the introducer sleeve assembly 102 can include a removable blunt tip obturator that can assist in atraumatic insertion in a patient's urethra.

Referring to FIGS. 2-3, one variation of the resecting device as described above has an electrode 145 with a resecting portion 149 that moves radially in an arc relative to axis 112 and a distal window 144. Another variation can provide an electrode 145 that reciprocates axially to move across the window 144 and would have similar effectiveness.

Referring back to FIG. 1, the electrode 145 comprises a first polarity electrode or active electrode and the shaft portion indicates that 245 comprise the return electrode.

Referring to FIG. 1, the resecting device 105 can be actuated by moveable finger grip 260 which is adapted to be squeezed toward fixed finger grip 262 to thus move the working end 115 and window surface WS axially back and forth to resect tissue. The physician can activate the electrosurgical function with a foot switch 265 (FIG. 1) and then reciprocate the working end 115 back and forth from about 5 mm to 25 mm to resect tissue in a path. At the same time, the physician can slightly rotate the shaft of the resecting device 105 so that the window surface WS engages a wider path in the targeted tissue surface.

In typical use, the physician would stabilize the sleeve portion 240 and endoscope 130, and then reciprocate and slightly rotate the resecting device 105 during a tissue resection procedure. During such a procedure, the physician can also slightly rotate the sleeve 240 and endoscope 130 to optimize viewing of the targeted tissue.

What is claimed is:

1. A tissue resecting device comprising:
   an elongated shaft having a central axis, a distal end, and a cylindrical outer surface,
   an offset housing fixed to one side on the cylindrical outer surface at the distal end of the elongated shaft, wherein the offset housing has an exterior surface with a tissue-receiving window therethrough, wherein the exterior surface of the offset housing is offset radially outwardly from the cylindrical outer surface of the elongated shaft; and
   a moveable electrode configured to move back and forth over the tissue-receiving window in a cutting envelope aligned with the exterior surface of the offset housing to resect tissue which extends into the tissue-receiving window, wherein the moveable electrode is configured to travel along an arc in a back-and-forth stroke in said cutting envelope.

2. The tissue resecting device of claim 1 wherein the moveable electrode is adapted to oscillate laterally over an exterior surface of the tissue-receiving window.

3. The tissue resecting device of claim 2 further comprising a motor coupled to the moveable electrode to oscillate the moveable electrode laterally over the exterior surface of the tissue-receiving window at a rate ranging from 1 Hz to 50 Hz.

4. The tissue resecting device of claim 3 further comprising a negative pressure source communicating through the elongated shaft with the tissue-receiving window.

5. The tissue resecting device of claim 4 further comprising a controller adapted to control at least one of an electrical source coupled to the moveable electrode, the motor coupled to the moveable electrode, and the negative pressure source.

6. The tissue resecting device of claim 5 wherein the controller is further adapted to control fluid inflows from a fluid source to a resection site.

7. The tissue resecting device of claim 2 wherein the exterior surface of the tissue-receiving window is offset outwardly from said cylindrical outer surface of the elongated shaft by at least 2 mm.

8. The tissue resecting device of claim 2 wherein the exterior surface of the tissue-receiving window is offset outwardly from said cylindrical outer surface of the elongated shaft by at least 4 mm.

9. The tissue resecting device of claim 2 wherein the exterior surface of the tissue-receiving window is offset outwardly from said cylindrical outer surface of the elongated shaft by a distance between 2 mm and 12 mm.

10. A tissue resecting device comprising:
   an elongated shaft extending within a cylindrical envelope about a central axis;
   a housing attached to a distal end of the elongated shaft, wherein the housing has an exterior surface with a tissue-receiving window therethrough and is positioned asymmetrically relative to the central axis; and
   a moveable electrode configured to move in a back-and-forth stroke over the tissue-receiving window in the housing in a cutting envelope aligned with the exterior surface of the housing to resect tissue, wherein the cutting envelope has an arc shape and is radially outwardly offset from the cylindrical envelope of the elongated shaft, wherein the moveable electrode moves across the arc-shaped cutting envelope.

11. The tissue resecting device of claim 10 wherein the asymmetric housing has an L-shape relative to the central axis.

12. The tissue resecting device of claim 10 wherein the exterior surface of the asymmetric housing is aligned in parallel to the central axis.

13. The tissue resecting device of claim 10 wherein the moveable electrode is adapted to move laterally over the cutting envelope.

14. The tissue resecting device of claim 10 wherein the moveable electrode is adapted to move axially over the cutting envelope.

15. The tissue resecting device of claim 10 further comprising a motor coupled to the moveable electrode to oscillate the moveable electrode over the cutting envelope.

16. The tissue resecting device of claim 15 wherein the motor is configured to oscillate the moveable electrode at a rate ranging from 1 Hz to 50 Hz.

17. The tissue resecting device of claim 10 wherein the cutting envelope has an arc shape.

18. The tissue resecting device of claim 10 wherein the tissue-receiving window has a rectangular shape.

19. The tissue resecting device of claim 10 wherein the tissue-receiving window has an axial dimension ranging from 2 mm to 20 mm.

20. The tissue resecting device of claim 10 wherein the tissue-receiving window has a lateral dimension ranging from 2 mm to 10 mm.

21. The tissue resecting device of claim 10 wherein the tissue-receiving window has spaced apart edges and the moveable electrode is configured to move past the edges.

22. The tissue resecting device of claim 10 wherein the tissue-receiving window has at least two sides with ledges for receiving the moveable electrode at a termination of its stroke.

23. A tissue resecting device comprising:
   an elongated shaft extending within a cylindrical envelope;
   a distal end of the elongated shaft fixedly coupled to an offset housing having a tissue-receiving window, wherein the tissue-receiving window has a cutting envelope with spaced-apart edges aligned with an exterior surface of the housing, wherein the cutting envelope is spaced outwardly from and oriented generally parallel to a cylindrical envelope of the elongated shaft; and
   a moveable electrode configured to move over the cutting envelope to resect tissue received through the tissue-receiving window, wherein the moveable electrode is configured to move past the spaced-apart edges of the tissue-receiving window when moved over the cutting envelope.

24. The tissue resecting device of claim 23 further comprising a motor coupled to the moveable electrode to oscillate the moveable electrode over the cutting envelope of the tissue-receiving window.

25. The tissue resecting device of claim 24 wherein the motor is configured to oscillate the moveable electrode at a rate ranging from 1 Hz to 50 Hz.

26. The tissue resecting device of claim 23 wherein the cutting envelope is offset radially outwardly from an outer surface of the elongated shaft by at least 2 mm.

27. The tissue resecting device of claim 26 wherein the cutting envelope is offset radially outwardly from the outer surface of the elongated shaft by at least 4 mm.

28. The tissue resecting device of claim 26 wherein the cutting envelope is offset radially outwardly from the outer surface of the elongated shaft by a distance in a range from 2 mm to 12 mm.

29. A tissue resecting device comprising:
   an elongated shaft having a working end with a tissue-receiving window, said elongated shaft having an outer surface extending within a cylindrical shaft envelope and said tissue-receiving window having an exterior surface extending over a cylindrical cutting envelope which is offset radially outwardly from the cylindrical shaft envelope; and
   a moveable electrode configured to move back-and-forth over the cutting envelope, wherein the cylindrical cutting envelope has an arc shape and wherein the moveable electrode is configured to move past spaced-apart edges of the tissue-receiving window when being moved over the cutting envelope.

30. The tissue resecting device of claim 29 further comprising a motor coupled to the moveable electrode to oscillate the moveable electrode laterally over the cylindrical cutting envelope.

31. The tissue resecting device of claim 30 wherein the motor is configured to oscillate the moveable electrode laterally over the cylindrical cutting envelope at a rate ranging from 1 Hz to 50 Hz.

32. The tissue resecting device of claim 31 wherein the cylindrical cutting envelope extends laterally in an arcuate shape.

33. The tissue resecting device of claim 32, wherein said moveable electrode moves in an arc over the cylindrical cutting envelope.

34. The tissue resecting device of claim 29 wherein the tissue-receiving window has a rectangular planar shape.

35. The tissue resecting device of claim 34 wherein the tissue-receiving window has an axial dimension ranging from 2 mm to 20 mm.

36. The tissue resecting device of claim 35 wherein the tissue-receiving window has a lateral dimension ranging from 2 mm to 10 mm.

37. The tissue resecting device of claim 29 wherein the tissue-receiving window has at least two sides with ledges for receiving the moveable electrode at a termination of its stroke.

38. The tissue resecting device of claim 29 wherein the tissue-receiving window is within a housing portion that is offset outwardly from an outer surface of the elongated shaft.

* * * * *